United States Patent [19]
Blondino et al.

[11] Patent Number: 6,004,537
[45] Date of Patent: Dec. 21, 1999

[54] PHARMACEUTICAL SOLUTION AEROSOL FORMULATIONS CONTAINING FLUOROALKANES, BUDESONIDE AND FORMOTEROL

[75] Inventors: Frank E. Blondino, Plantation; Michael Brucato, Miami Shores; Maria W. Buenafe, Miami Beach; Kelly A. Cavanaugh, Homestead, all of Fla.

[73] Assignee: Baker Norton Pharmaceuticals, Inc., Miami, Fla.

[21] Appl. No.: 09/215,280

[22] Filed: Dec. 18, 1998

[51] Int. Cl.$^6$ .................................................. A61K 9/12
[52] U.S. Cl. ................................. 424/45; 424/46
[58] Field of Search .......................... 424/45, 46

[56] References Cited

U.S. PATENT DOCUMENTS

| | | |
|---|---|---|
| 4,174,295 | 11/1979 | Bargigia et al. . |
| 5,190,029 | 3/1993 | Byron et al. . |
| 5,225,183 | 7/1993 | Purewal et al. . |
| 5,605,674 | 2/1997 | Purewal et al. . |
| 5,653,962 | 8/1997 | Akehurst et al. . |
| 5,674,471 | 10/1997 | Akehurst et al. . |
| 5,674,473 | 10/1997 | Purewal et al. . |
| 5,683,677 | 11/1997 | Purewal et al. . |
| 5,695,743 | 12/1997 | Purewal et al. . |
| 5,776,432 | 7/1998 | Schultz et al. . |

FOREIGN PATENT DOCUMENTS

| | | |
|---|---|---|
| 0 550 031 | 7/1993 | European Pat. Off. . |
| 0 553 298 | 11/1994 | European Pat. Off. . |
| 41 23 663 | 1/1993 | Germany . |
| WO92/22286 | 12/1992 | WIPO . |
| WO93/11773 | 6/1993 | WIPO . |
| WO97/47286 | 12/1997 | WIPO . |

*Primary Examiner*—Raj Bawa
*Attorney, Agent, or Firm*—Jeffrey S. Melcher; Farkas & Manelli, PLLC

[57] ABSTRACT

Provided is a solution aerosol formulation adapted for use in a pressurized aerosol container. The aerosol formulation is formulated from a composition containing Budesonide, Formoterol at least one fluoroalkane propellant, and a cosolvent present in an amount that dissolves or solubilizes the Budesonide and Formoterol in the mixture of cosolvent and propellant.

30 Claims, No Drawings

6,004,537

PHARMACEUTICAL SOLUTION AEROSOL FORMULATIONS CONTAINING FLUOROALKANES, BUDESONIDE AND FORMOTEROL

FIELD OF THE INVENTION

The invention relates to pharmaceutical aerosol formulations containing Budesonide and Formoterol dissolved or solubilized in a fluoroalkane(s) and a cosolvent(s).

BACKGROUND OF THE INVENTION

Chlorohydrocarbon and chlorofluorocarbon propellants used in medical aerosol formulations are generally considered to be environmentally unfriendly. Therefore, these propellants have been largely replaced by hydrofluoroalkanes such as 1,1,1,2 tetrafluoroethane ("HFA -134a") and 1,1,1,2,3,3,3 heptafluoropropane ("HFA-227ea") that have been identified as safe for use in pressurized metered dose inhalers.

Medicinal aerosol formulations are generally of the solution or suspension type. Each type is composed of at least the medicament and the propellant. The solution type aerosol formulation contains the medicament dissolved or solubilized in the propellant, or a mixture of propellant and cosolvent. The suspension type aerosol formulation contains the medicament in the form of particles which are dispersed in the propellant. The suspension type aerosol formulations usually contains a surfactant, and can also include a cosolvent. Conventional Budesonide aerosol formulations are of the suspension type. Conventional Formoterol aerosol formulations are of the solution and suspension type.

U.S. Pat. No. 5,736,124 (Akehurst) discloses a suspension type aerosol formulation in which the medicament is in the form of particles dispersed in a cosolvent. The cosolvent is present in an amount less than 5% by weight to avoid dissolving the medicament (column 4, lines 13–24).

Published International Application No. WO 98/05302 discloses a suspension type aerosol formulation in which the medicament is in the form of particles dispersed in a cosolvent. The cosolvent can be present in amount of from 6 to 25% by weight. However, this application teaches that the medicament and cosolvent selected should be such that the medicament is not dissolved in the cosolvent and the particulate shape of the medicament is retained.

Ethanol has been used as a cosolvent. However, previous teachings such as European Patent No. EP 0 616525 have taught away from using concentrations of ethanol greater than 5% in solution aerosol formulations for β-agonists.

Each of the drugs Budesonide and Formoterol has proven difficult to formulate into conventional aerosol compositions. Such formulations have exhibited short shelf-lives and require refrigeration. Refrigeration is undesirable because many patients are required to carry the aerosol canisters on their persons. There remains, therefore, an important need for aerosol formulations containing Budesonide and Formoterol that remain chemically and physically stable during storage at ambient conditions of temperature and humidity.

SUMMARY OF THE INVENTION

An objective of the present invention is to provide a pressurized metered dose inhaler containing a stable solution formulation of Budesonide and Formoterol which does not require the use of refrigeration.

Another objective of the present invention is to provide a stable solution formulation of Budesonide and Formoterol that is suitable for use as an aerosol, which does not require the use of refrigeration.

The above objectives and other objectives are surprisingly achieved by the following. The present invention provides a novel pressurized metered dose inhaler comprising a container equipped with a metering valve and containing a pressurized solution aerosol formulation formulated from a composition comprising:

Budesonide;

Formoterol;

at least one fluoroalkane propellant; and a cosolvent present in an amount that dissolves or solubilizes the Budesonide and Formoterol in the mixture of cosolvent and propellant.

The present invention also provides a novel solution aerosol formulation formulated from a composition comprising:

Budesonide;

Formoterol;

at least one fluoroalkane propellant; and a cosolvent present in an amount that dissolves or solubilizes the Budesonide and Formoterol in the mixture of cosolvent and propellant.

DETAILED DESCRIPTION OF PREFERRED EMBODIMENTS

It has been unexpectedly discovered that chemically and physically stable aerosol formulations containing a mixture of Budesonide and Formoterol can be formulated utilizing high concentrations of cosolvent in which the mixture of Budesonide and Formoterol is dissolved or solubilized in the mixture of cosolvent and propellant. Budesonide and Formoterol aerosol formulations can be formed according to the present invention which exhibit enhanced stability under elevated temperatures (40° C.), thus requiring no refrigeration. The term "Formoterol" is hereinafter understood to mean the base form of Formoterol as well as the weak acid form of Formoterol, unless stated otherwise. A preferred weak acid form of Formoterol is Formoterol fumarate. When Formoterol fumarate is utilized in combination with Budesonide, the amount is usually from about 0.01 to about 0.5% by weight, preferably about 0.01 to about 0.1% by weight. All weight percents are based on the total weight of the formulation unless stated otherwise.

The amount of Budesonide utilized in the present solution type aerosol formulations is usually from about 0.01 to about 1% by weight, preferably about 0.05 to about 0.5% by weight, and most preferably about 0.3% by weight, based on the total weight of the aerosol formulation.

Any cosolvent that is suitable for inhalation and capable of dissolving or solubilizing the mixture of Budesonide and Formoterol in the mixture of cosolvent and propellant can be used. Examples of suitable cosolvents include alcohols, ethers, hydrocarbons, and perfluorocarbons. Preferably, the cosolvent is a short chain polar alcohol. More preferably, the cosolvent is an aliphatic alcohol having from one to six carbon atoms, such as ethanol or isopropanol. The most preferred cosolvent is ethanol. Examples of suitable hydrocarbons include n-butane, isobutane, pentane, neopentane and isopentanes. Examples of suitable ethers include dimethyl ether and diethyl ether. Examples of suitable perfluorocarbons include perfluoropropane, perfluorobutane, perfluorocyclobutane, and perfluoropentane.

When ethanol is utilized as the cosolvent, the cosolvent is usually present in an amount of from about 6% to about 40% by weight, based on the total weight of the aerosol formulation. The ethanol should be present in an amount which fully dissolves or solubilizes Budesonide and Formoterol in the mixture of ethanol and propellant. Preferably, ethanol is present in amount sufficient to fully maintain the Budesonide and Formoterol in solution at freezing temperatures, such as 0° C. In general, as the temperature is decreased, the solubility of Budesonide and Formoterol in ethanol is decreased. Therefore, an excess of ethanol over the amount required to fully dissolve or solubilize Budesonide and Formoterol at ambient or room temperature is preferred. In this regard, ethanol is preferably present in an amount of at least 10% by weight, more preferably at least 15% by weight, even more preferably at least 20% by weight, and most preferably at least 25% by weight. Based on the disclosure provided herein, one skilled in the art will recognize that lower concentrations of medicament usually require lower concentrations of cosolvent, and vice versa, in order to form a stable solution. Furthermore, one skilled in the art will recognize that the type of propellant utilized can also affect the amount of ethanol required to fully dissolve or solubilize Budesonide and Formoterol in the mixture of ethanol and propellant. In general, the greater the polarity of the propellant the less ethanol required to fully dissolve or solubilize Budesonide and Formoterol. For example, when HFA-134a is utilized as the propellant, the amount of ethanol is preferably from about 10 to about 30% by weight. When HFA-227ea is utilized, preferred amounts of ethanol are from about 6 to about 20% by weight.

Any fluoroalkane propellant that is suitable for inhalation can be used. Examples of suitable fluoroalkanes include HFA-134a, HFA-227ea, HFA-125 (pentafluoroethane), HFA-152a (1,1-difluoroethane), and HFA-32 (difluoromethane). Hydrocarbon and/or aliphatic gases may be added to modify propellant characteristics as required. Preferably, the aerosol formulation is substantially free of chlorofluorocarbons. However, if desired chlorofluorocarbons can be utilized. Preferably, the fluoroalkane is 1,1,1,2-tetrafluoroethane (HFA-134a) or 1,1,1,2,3,3,3-heptafluoropropane (HFA-227ea). Most preferably, only a single fluoroalkane is utilized as the propellant.

The propellant is usually present in an amount of from about 60% to about 94% by weight, preferably from about 70 to about 90% by weight, based on the total weight of the aerosol formulation.

A preferred aerosol formulation comprises HFA-134a or HFA-227ea in an amount less than about 90% by weight, ethanol in an amount of at least about 10% by weight, Budesonide in an amount of from about 0.05 to 0.5% by weight, and Formoterol fumarate in an amount of from about 0.01 to about 0.1% by weight. A particularly preferred aerosol formulation comprises about 75% by weight of HFA-134a, about 25% by weight of ethanol, about 0.3% by weight of Budesonide, and about 0.01% by weight of Formoterol fumarate. The aerosol formulation is preferably free of surfactants.

Pressurized metered dose inhalers are now well known in the art. Any pressurized metered dose inhaler that is suitable for application of medicaments to the lungs or nose of a patient can be used. Pressurized metered dose inhalers usually are equipped with an actuator having a spray orifice diameter of about 460 μm. However, with the higher concentrations of solvent employed in the present invention, it may be desirable that the solvent evaporates as soon as possible after inhalation. This can be achieved by reducing particle size by reducing the spray orifice diameter, for example, to 250 μm, in combination with using solvent concentrations greater than about 10% by weight. Based on the disclosure provided herein, one skilled in the art will be able to adjust the component composition to deliver a desired dose for the selected metered valve, without undue experimentation. For example, the composition may be altered to adjust the vapor pressure of the formulation. The aerosol formulation and metering valve are usually selected to provide a therapeutically effective amount of the Budesonide and Formoterol per activation. An example of a therapeutically effective amount of Budesonide is about 50 to about 400 μg per activation, preferably about 150 to about 250 μg per activation. An example of a therapeutically effective amount of Formoterol fumarate when used in combination with Budesonide has been found to be about 1 to about 50 μg per activation, preferably about 5 to about 25 μg per activation.

The pressurized metered dose inhaler can be formed by any suitable method. For example, the selected amount of Budesonide and Formoterol can be weighed and inserted into a suitable container, such as a plastic coated glass bottle or aluminum canister. The cosolvent can then be weighed and added to the container. Once all of the non-gaseous components have been added to the container, the metered valve can be crimped on to seal the container. Then, the desired amount of propellant can be added to the container through the metered valve. The Budesonide and Formoterol can be dissolved or solubilized into the mixture of cosolvent and propellant by agitating the formulation, such as by sonication. About 5 minutes of sonication has been found to be suitable to fully dissolve or solubilize a formulation having a total weight of about 13 grams.

The present invention will now be explained with reference to the following non-limiting examples.

EXAMPLES 1–4

Four solution aerosols compositions according to the present invention were formulated by combining the components shown in Tables I and II, using the following steps:
1. Weighing the cosolvent into a plastic coated glass bottle or an aluminum canister.
2. Adding the weighed medicaments.
3. Crimping a valve upon the bottle or canister.
4. Adding a known amount of propellant through the valve into the bottle or canister.
5. Sonicating the formulation for about 5 minutes.

The formulations were tested using the following three very well known methods and the Pharmacopeia Forum, vol. 22, no. 6 standards:
(1) Andersen Multistage Cascade Impactor;
(2) Single Stage Liquid Impinger; and
(3) Unit Spray.

Table III discloses the test results of the Example 1 and 2 formulations using the Unit Spray analysis. These results indicate reproducible dosing throughout the product's life. No significant degradation of medicaments or impurities were observed during these tests.

Table VI discloses the test results of the Examples 3 and 4 formulations using a Unit Spray Analysis, in which the formulations were stored in an oven at 40° C. for 5 days. The test results in Table VI demonstrate that the Budesonide and Formoterol aerosol formulations according to the present invention are remarkably stable at elevated temperatures and therefore do not require refrigeration. The test results also demonstrate that about 10% of the medicament was retained on the actuator and about 90% of the medicament was dispensed to the dose tube, which represents that the composition is acceptable for use as an aerosol formulation.

Table V discloses the test results of the Example 3 formulation using an Andersen Multistage Cascade Impactor for the beginning, middle and end of can. These test results demonstrate that the solution formulation according to the present invention is suitable for application to the lungs. The stages 2 through F represent medicament that is capable of reaching the lungs from a conventional applicator. A total medicament amount of about 30% for stages 2 through F is considered good. As can be seen from Table V, the beginning and middle of the can for both Formoterol and Budesonide each exhibited a total medicament amount of about 30% for the stages 2 through F.

TABLE 1

| | Component | Weight (g) | % |
|---|---|---|---|
| Example 1 | Formoterol | 0.001517 | 0.011 |
| | Budesonide | 0.03855 | 0.28 |
| | Ethanol | 2.22 | 16.5 |
| | HFA-134a | 11.207 | 83.2 |
| Example 2 | Formoterol | 0.001194 | 0.0099 |
| | Budesonide | 0.03910 | 0.32 |

TABLE 1-continued

| Component | Weight (g) | % |
|---|---|---|
| Ethanol | 2.280 | 18.8 |
| HFA-134a | 9.7904 | 80.8 |

TABLE II

| | | | |
|---|---|---|---|
| Example 3 | Formoterol | 0.0012396 | 0.0090 |
| | Budesonide | 0.04322 | 0.31 |
| | Ethanol | 3.4026 | 24.7 |
| | HFA-134a | 10.3515 | 75.0 |
| Example 4 | Formoterol | 0.001293 | 0.0096 |
| | Budesonide | 0.04287 | 0.32 |
| | Ethanol | 3.49130 | 25.9 |
| | HFA-134a | 9.97050 | 76.3 |

TABLE III

| | Example 1 (Stored in Oven for 9 days) | | | Example 2 (Room Temperature) | | |
|---|---|---|---|---|---|---|
| | Unit Spray Content | | | | | |
| Test | Shot numbers | Formoterol (%) | Budesonide (%) | Shot numbers | Formoterol (%) | Budesonide (%) |
| Test 1 | 1–20 | 71 | 92 | 1–20 | 83 | 96 |
| Test 2 | 21–40 | 74 | 95 | 21–40 | 87 | 95 |
| Test 3 | 41–60 | 76 | 99 | 41–60 | 88 | 98 |
| Test 4 | 61–80 | 77 | 99 | 61–80 | 87 | 98 |
| Test 5 | 81–100 | 76 | 94 | 81–100 | 88 | 94 |
| Test 6 | 101–120 | 75 | 95 | 101–120 | 88 | 97 |
| Test 7 | 121–140 | 79 | 97 | 121–140 | 90 | 100 |
| Test 8 | 141–160 | 80 | 100 | 141–160 | 99 | 104 |
| | Average | 76 | 96 | Average | 89 | 98 |

TABLE IV

| | Example 3 | | | Example 4 | | |
|---|---|---|---|---|---|---|
| | Unit Spray Content | | | | | |
| Test | Shot numbers | Formoterol (%) | Budesonide (%) | Shot numbers | Formoterol (%) | Budesonide (%) |
| Test 1 | 3–4 | 74 | 94 | 3–4 | 82 | 88 |
| Test 2 | 5–6 | 76 | 95 | 5–6 | 87 | 92 |
| Test 3 | 27–28 | 83 | 91 | | na | na |
| Test 4 | 29–30 | 84 | 92 | | na | na |
| Test 5 | 111–112 | 87 | 96 | | na | na |
| Test 6 | 113–114 | 87 | 97 | | na | na |
| | Average | 82 | 94 | Average | 85 | 90 |

TABLE V

|  | Formoterol | | | | | | Budesonide | | | | | |
|---|---|---|---|---|---|---|---|---|---|---|---|---|
|  | (Beginning) | | (Middle) | | (End) | | (Beginning) | | (Middle) | | (End) | |
|  | Amt. ($\mu$g) | Amt. (%) | Amt. ($\mu$g) | Amt. (%) | Amt. ($\mu$g) | Amt. (%) | Amt. ($\mu$g) | Amt. (%) | Amt. ($\mu$g) | Amt. (%) | Amt. ($\mu$g) | Amt. (%) |
| Actuator | 10.5 | 9.6 | 7.84 | 7.1 | 17.2 | 16.0 | 398.4 | 9.8 | 290.6 | 6.90 | 659.8 | 15.0 |
| Valve | 0.6 | 0.5 | 0.63 | 0.6 | 0.7 | 0.6 | 22.7 | 0.6 | 16.1 | 0.38 | 0.0 | 0.0 |
| Induction Port | 54.8 | 50.0 | 61.4 | 55.8 | 58.1 | 53.9 | 2162.0 | 53.3 | 2364.7 | 56.11 | 2449.1 | 55.5 |
| Stage 0 | 6.2 | 5.6 | 5.2 | 4.7 | 7.5 | 7.0 | 235.8 | 5.8 | 213.3 | 5.06 | 324.3 | 7.4 |
| Stage 1 | 1.9 | 1.7 | 1.5 | 1.4 | 1.2 | 1.1 | 75.9 | 1.9 | 66.7 | 1.58 | 90.0 | 2.0 |
| Stage 2 | 0.7 | 0.7 | 0.9 | 0.8 | 0.4 | 0.4 | 19.1 | 0.5 | 25.9 | 0.62 | 22.5 | 0.5 |
| Stage 3 | 1.5 | 1.4 | 2.3 | 2.1 | 1.0 | 1.0 | 55.6 | 1.4 | 89.5 | 2.12 | 52.7 | 1.2 |
| Stage 4 | 7.2 | 6.6 | 7.3 | 6.6 | 5.5 | 5.1 | 271.5 | 6.7 | 281.7 | 6.68 | 226.0 | 5.1 |
| Stage 5 | 15.4 | 14.0 | 13.5 | 12.3 | 8.2 | 7.6 | 443.1 | 10.9 | 498.5 | 11.83 | 235.8 | 5.4 |
| Stage 6 | 5.6 | 5.1 | 4.7 | 4.3 | 4.4 | 4.1 | 175.8 | 4.3 | 178.2 | 4.23 | 179.6 | 4.1 |
| Stage 7 | 2.8 | 2.5 | 2.0 | 1.8 | 1.6 | 1.5 | 95.5 | 2.4 | 81.3 | 1.93 | 85.4 | 1.9 |
| Stage F | 2.5 | 2.3 | 2.8 | 2.5 | 1.9 | 1.8 | 102.7 | 2.5 | 108.1 | 2.56 | 85.4 | 1.9 |
| Total Drug | 109.5 | 100 | 110 | 100 | 107.8 | 100 | 4058.1 | 100 | 4214.6 | 100 | 4410.7 | 100 |
| No Shots | 20 | | 20 | | 20 | | 20 | | 20 | | 20 | |
| Avg. Shot Weight | 68.23 | | 68.23 | | 68.28 | | 68.23 | | 68.23 | | 68.28 | |
| Actual Dose Delivered ($\mu$g/actuation) | 5.47 | | 5.51 | | 5.39 | | 202.90 | | 210.73 | | 220.53 | |
| Material Balance (%) | 89 | | 90 | | 88 | | 95 | | 99 | | 103 | |
| MMAD (microns) | 2.0 | | 2.0 | | 2.4 | | 2.1 | | 2.0 | | 2.6 | |
| GSD | 2.6 | | 2.6 | | 3.0 | | 2.9 | | 2.7 | | 3.5 | |
| Fine Particle Dose ($\mu$g) | 36 | | 34 | | 23 | | 1163 | | 1263 | | 887 | |
| Fine Particle Fraction (%) | 37 | | 33 | | 26 | | 32 | | 32 | | 24 | |

While the claimed invention has been described in detail and with reference to specific embodiments thereof, it will be apparent to one of ordinary skill in the art that various changes and modifications can be made to the claimed invention without departing from the spirit and scope thereof.

We claim:

1. A pressurized metered dose inhaler comprising a container equipped with a metering valve and containing a pressurized solution aerosol formulation formulated from a composition comprising:

about 0.01 to about 1% by weight of Budesonide;
   about 0.01 to about 0.5% by weight of Formoterol;
   about 60 to about 94% by weight of at least one fluoroalkane propellant; and
   a cosolvent present in an amount that dissolves or solubilizes said Budesonide and Formoterol in the mixture of cosolvent and propellant, wherein said cosolvent is at least one selected from the group consisting of alcohols, ethers, hydrocarbons and perfluorocarbons.

2. A solution aerosol formulation adapted for use in a pressurized aerosol container, said aerosol formulation being formulated from a composition comprising:

about 0.01 to about 1% by weight of Budesonide;
   about 0.01 to about 0.5% by weight of Formoterol;
   about 60 to about 94% by weight of at least one fluoroalkane propellant; and
   a cosolvent present in an amount that dissolves or solubilizes said Budesonide and Formoterol in the mixture of cosolvent and propellant, wherein said cosolvent is at least one selected from the group consisting of alcohols, ethers, hydrocarbons and perfluorocarbons.

3. A pressurized metered dose inhaler according to claim 1, wherein said cosolvent comprises ethanol.

4. A pressurized metered dose inhaler according to claim 2, wherein said ethanol is present in an amount of at least 10% by weight.

5. A pressurized metered dose inhaler according to claim 2, wherein said ethanol is present in an amount of at least 15% by weight.

6. A pressurized metered dose inhaler according to claim 2, wherein said ethanol is present in an amount of at least 20% by weight.

7. A pressurized metered dose inhaler according to claim 2, wherein said ethanol is present in an amount of at least 25% by weight.

8. A pressurized metered dose inhaler according to claim 1, wherein said formulation is free of a surfactant.

9. A pressurized metered dose inhaler according to claim 1, wherein said propellant comprises 1,1,1,2-tetrafluoroethane or 1,1,1,2,3,3,3-heptafluoropropane.

10. A pressurized metered dose inhaler according to claim 1, wherein said Budesonide is present in an amount of from about 0.01 to about 1% by weight and said Formoterol is present in an amount of from about 0.01 to about 0.5% by weight, based on the total weight of the composition.

11. A pressurized metered dose inhaler according to claim 1, wherein said formulation is substantially free of chlorofluorocarbons.

12. A pressurized metered dose inhaler according to claim 1, wherein said propellant is present in an amount of from about 70 to about 94% by weight.

13. A pressurized metered dose inhaler according to claim 1, wherein said cosolvent is present in an amount sufficient to maintain said Budesonide and Formoterol in solution at 0° C.

14. A pressurized metered dose inhaler according to claim 1, wherein said cosolvent comprises an aliphatic alcohol having from 1 to about 6 carbon atoms.

15. A pressurized metered dose inhaler according to claim 1, wherein said Budesonide is present in an amount of about 0.05 to about 0.5% by weight, said Formoterol is present in an amount of about 0.01 to about 0.1% by weight, said cosolvent comprises ethanol in an amount of about 10 to about 40% by weight, and said propellant is present in an amount of from about 60% to about 90% by weight, all weights based on the total weight of said aerosol formulation.

16. A pressurized metered dose inhaler according to claim 1, wherein said aerosol formulation is adapted to be stable under conditions up to about 40° C. and about 75% relative humidity for at least about four weeks.

17. A solution aerosol formulation according to claim 2, wherein said cosolvent comprises ethanol.

18. A solution aerosol formulation according to claim 17, wherein said ethanol is present in an amount of at least 10% by weight.

19. A solution aerosol formulation according to claim 17, wherein said ethanol is present in an amount of at least 15% by weight.

20. A solution aerosol formulation according to claim 17, wherein said ethanol is present in an amount of at least 20% by weight.

21. A solution aerosol formulation according to claim 17, wherein said ethanol is present in an amount of at least 25% by weight.

22. A solution aerosol formulation according to claim 2, wherein said formulation is free of a surfactant.

23. A solution aerosol formulation according to claim 2, wherein said propellant comprises 1,1,1,2-tetrafluoroethane or 1,1,1,2,3,3,3-heptafluoropropane.

24. A solution aerosol formulation according to claim 2, wherein said Budesonide is present in an amount of from about 0.01 to about 1% by weight, based on the total weight of the composition and said Formoterol is present in an amount of about 0.01 to about 0.5% by weight.

25. A solution aerosol formulation according to claim 2, wherein said formulation is substantially free of chlorofluorocarbons.

26. A solution aerosol formulation according to claim 2, wherein said propellant is present in an amount of from about 70 to about 94% by weight.

27. A solution aerosol formulation according to claim 2, wherein said cosolvent is present in an amount sufficient to maintain said Budesonide and Formoterol in solution at 0° C.

28. A solution aerosol formulation according to claim 2, wherein said cosolvent comprises an aliphatic alcohol having from 1 to about 6 carbon atoms.

29. A solution aerosol formulation according to claim 2, wherein said Budesonide is present in an amount of about 0.05 to about 0.5% by weight, said Formoterol is present in an amount of about 0.01 to about 0.1% by weight, said cosolvent comprises ethanol in an amount of about 10 to about 40% by weight, and said propellant is present in an amount of from about 60% to about 90% by weight, all weights based on the total weight of said aerosol formulation.

30. A solution aerosol formulation according to claim 2, wherein said aerosol formulation is adapted to be stable under conditions up to about 40° C. and about 75% relative humidity for at least about four weeks.

* * * * *